United States Patent
Gernon et al.

(12)

(10) Patent No.: US 6,187,169 B1
(45) Date of Patent: Feb. 13, 2001

(54) GENERATION OF ORGANOSULFONIC ACID FROM ITS SALTS

(75) Inventors: Michael D. Gernon, Montgomery; Nicholas M. Martyak, Doylestown; Martin Nosowitz, Chester; Gary S. Smith, Upper Providence Township, Montgomery County, all of PA (US)

(73) Assignee: ATOFINA Chemicals, Inc., Philadelphia, PA (US)

( * ) Notice: Under 35 U.S.C. 154(b), the term of this patent shall be extended for 0 days.

(21) Appl. No.: 09/288,266

(22) Filed: Apr. 8, 1999

Related U.S. Application Data

(63) Continuation-in-part of application No. 08/918,736, filed on Aug. 19, 1997, now abandoned, which is a continuation-in-part of application No. 08/798,985, filed on Feb. 11, 1997, now abandoned.
(60) Provisional application No. 60/026,371, filed on Sep. 16, 1996.

(51) Int. Cl.[7] ................. C25B 3/00; C25C 1/00; C25C 1/20; C25C 1/10; C07C 309/00
(52) U.S. Cl. ............ 205/445; 205/560; 205/565; 205/573; 205/574; 205/587; 205/602; 562/30; 562/41; 562/118; 562/124
(58) Field of Search ............... 205/445, 560, 205/565, 573, 574, 587, 597, 602, 610; 562/30, 41, 118, 124

(56) References Cited

U.S. PATENT DOCUMENTS 5,520,794  *  5/1996  Gernon .................. 205/598

FOREIGN PATENT DOCUMENTS 8-71376  *  3/1996  (JP) .

* cited by examiner

*Primary Examiner*—Edna Wong
(74) *Attorney, Agent, or Firm*—Stanley A. Marcus; Gilbert W. Rudman

(57) ABSTRACT

A procedure for the generation of organosulfonic acids from solutions of corresponding metal organosulfonate compounds by electrowinning, electrolytically driven hydrolysis or chemically driven hydrolysis is described. Appropriate organosulfonate compounds include the water soluble salts of alkanesulfonic and aromatic sulfonic acids which incorporate metals from Group VIB, VIIB, VIIIB, IB, IIB or VA of the periodic table. The electrowinning and electrolytic techniques described can be applied in divided or undivided cells and can be operated in continuous fashion to provide the greatest efficiency. Hydrolysis based methods can employ either anodic oxidation or oxidation both of which function to oxidize the metal cation(s) present to hydrolytically unstable higher oxidation states.

24 Claims, No Drawings

GENERATION OF ORGANOSULFONIC ACID FROM ITS SALTS

CROSS REFERENCES TO RELATED APPLICATIONS

This application is a continuation-in-part of U.S. application Ser. No. 08/918,736, filed Aug. 19, 1997, now abandoned, which is a continuation-in-part of U.S. application Ser. No. 08/798,985, filed Feb. 11, 1997, now abandoned, which claimed the benefit of U.S. Provisional Application Ser. No. 60/026,371, filed Sep. 16, 1996.

FIELD OF THE INVENTION

This invention is an efficient and economical method for the generation of substantially pure forms of alkanesulfonic or aromatic sulfonic acids (hereinafter sometimes referred to as organosulfonic acid or sulfonic acid) from solutions of corresponding organosulfonate compounds of VIB, VIIB, VIIIB, IB, IIB and/or VA metals. The method involves either the electrowinning of a solution of the metal salt and/or the hydrolytic generation of acid through oxidation of the metal cation. A combination of electrowinning and hydrolysis can also be used.

BACKGROUND OF THE INVENTION

Electrowinning systems for the recovery of metals from salt solutions are well known. In most systems of this type, the intent is to dispose of spent electrolyte solutions as waste and/or to recover metal value for reuse. In some cases, a limited incidental amount of recovery of acid value is obtained in conjunction with related processes. A procedure is disclosed in U.S. Pat. No. 4,944,851 for the regeneration of a spent tin/lead stripping composition comprising an aqueous solution of an alkanesulfonic acid, metal alkanesulfonate salts and metal nitrate salts by electrolyzing the solution and thus removing certain metal salts at the cathode while regenerating other metal salts along with some acid at the anode. In this system, inorganic nitrate is an essential component of the solution since it is required to act upon the tin-lead layer to effect its removal from the substrate. The procedure described pertains only to the regeneration of stripping capacity in solutions which contain at a minimum both metal alkanesulfonate salts and metal nitrate salts. The objective of the process, as stated by the inventors, is specifically to restore the stripping effectiveness of two-component compositions. The process of the aforementioned U.S. Pat. No. 4,944,851 is not designed to generate sulfonic acid which may have general application in electrolytic and/or other processes as well as in the process from which the sulfonic acid was originally obtained.

U.S. Pat. No. 5,520,794 by Gernon discloses the use of an undivided cell electrowinning process for the recovery of methanesulfonic acid value from a solution of plumbous methanesulfonate. However, when an electrowinning process is carried out, as described by Gernon, in an undivided cell, then the resulting acid product has poor purity owing mostly to contamination by some residue of the metal(s) originally present.

The applications in which such poor purity MSA can be used are usually somewhat restricted.

Vork (Tijdschr. Oppervlaktetech. Corrosiebestrijd. 1995, 39(6), 242–4) discloses the use of an anion-exchange membrane divided electrowinning cell for the recovery of pure methanesulfonic acid from methanesulfonic acid based tin/lead plating solutions. The methanesulfonic acid recovered by Vork was sufficiently pure to be of value for general use, for instance, as an acid catalyst in a number of esterification reactions.

It would be useful to have a general process for obtaining alkanesulfonic acid value and/or pure alkanesulfonic acid from an aqueous solution containing one or more VIB, VIIB, VIII, IB, IIB and/or VA metal alkanesulfonates. Neither such a process nor the possibility for general acid recovery from metal alkanesulfonates are disclosed in the prior art, except for the distinct IVA metal salts tin and lead methanesulfonate.

An element's physical and chemical properties are related to the element's position in the periodic table and since tin and lead are in the same family of the Periodic Table (i.e., the IVA metals) they have certain similarities in physical and chemical properties which are not common to metals outside of group IVA.

Also, in electrowinning processes for the recovery of alkanesulfonic acid value or pure alkanesulfonic acid from aqueous solutions containing metal alkanesulfonates, the specific metal alkanesulfonate involved strongly influences the many operational parameters present (e.g., electrode material selection, membrane selection, membrane fouling prevention schemes, metal hydrolysis accommodation, etc.). Thus, a process designed for tin methanesulfonate and/or lead methanesulfonate does not simply extrapolate to the whole of the periodic table.

Therefore, though it has previously been shown that methanesulfonic acid can be recovered from tin methanesulfonate and lead methanesulfonate under certain conditions, it is not known generally that alkanesulfonic acid can be recovered from other electrodepositable metals (namely metals in groups VIB, VIIB, VIII, IB, IIB and VA).

SUMMARY OF THE INVENTION

This invention is a process for the generation of alkanesulfonic or aromatic sulfonic acids from their soluble salts of metals of Group VIB, VIIB, VIIIB, IB, IIB or VA of the periodic table comprising subjecting an inorganic nitrate-free solution of said salt to:

a) electrowinning in a cell employing a reactive cathode and an anode, electrogenerating, within an effective current density range, an alkanesulfonic or aromatic sulfonic acid from said salt at said anode and electrolytically producing a metal or metal compound from said salt adjacent to or on said cathode, and substantially removing any metal containing precipitate from said solution, wherein the cell is undivided when the soluble salts are of metals of Group VA of the periodic table; or b) electrolysis in a cell employing a reactive cathode and an anode, electrogenerating an oxidized species at said anode with said oxidized species reacting further to produce a sulfonic acid and a metal containing precipitate, and substantially removing said metal precipitate from the solution, or c) a chemical oxidizing agent in an amount sufficient to create an oxidized species which reacts further to produce a sulfonic acid along with a metal containing precipitate, and substantially removing said metal containing precipitate from said solution, or d) any combination of a), b) and c).

In a preferred embodiment the present invention is directed to (a) the recovery of alkanesulfonic acid value from VIB, VIIB, VIII, IB, IIB and VA (i.e., Cr, Mo, W, Mn, Tc, Re, Fe, Co, Ni, Ru, Rh, Pd, Os, Ir, Pt, Cu, Ag, Au, Zn, Cd, Hg, As, Sb, Bi) metal alkanesulfonates by electrowinning in an undivided cell, and (b) the recovery of pure alkanesulfonic acid from metal alkanesulfonates, defined as described above for a, by electrowinning in an anion-exchange membrane separated cell. The present invention describes how, in general, to obtain either alkanesulfonic acid value or pure alkanesulfonic acid from select metal alkanesulfonates, as defined above, which can be electrodeposited from an aqueous solution. The present invention also describes when a divided cell process versus an undivided cell process is truly necessary.

In the electrowinning reaction referred to above, the sulfonic acid is regenerated at the anode by electrochemical reaction while the metal cation of the salt is taken up at the cathode by electrodeposition of the metal and/or by the formation of some other type of metal containing precipitate (e.g., sludge) adjacent to the cathode. In the electrolysis reaction referred to above in b), sulfonic acid and metal oxide/hydroxide type compounds are formed at or near the anode by hydrolytic reactions of anodically produced higher oxidation states of the metal cation of the salt.

While the term "electrowinning" is normally intended to cover electrolytic processing of an electrolyte to form a pure metal on or near the reactive cathode of the system, as used herein, "electrowinning" also includes processes wherein the formation of insoluble metal oxide type species, a process sometimes referred to as "sludging", occurs at or near the cathode. To efficiently run an electrowinning system which operates with a significant amount of sludging, a divided cell must be employed so as to prevent the intermixing of anodically generated acid with cathodically generated base.

DETAILED DESCRIPTION OF THE INVENTION

This invention provides a method for the generation of one or more organosulfonic acids which are alkanesulfonic or aromatic sulfonic acids from a solution of the corresponding metal organosulfonates. Useful acid generation can be obtained from solutions of all those organosulfonate compounds which can be formed from the metals of Group VIB, VIIB, VIIIB, IB, IIB or VA of the periodic table of the elements. Such salts include, e.g., the Mn(II), Fe(II), Fe(III), Co(II), Ni(II), Pd(II), Pt(II), Cu(II), Ag(I), Ir(IV), Ru(III), Rh(III), Co(II), Au(I), Zn(II) and Bi(III) salts of methanesulfonic acid (MSA), ethanesulfonic acid (ESA) and/or p-toluenesulfonic acid, among others. The alkanesulfonate portion of the salts from which alkanesulfonic acid value may be recovered may be composed of substituted or unsubstituted linear or branched chains of 1 to 8 carbon atoms with monosulfonate or polysulfonate functionalization and with the possibility of further functionalization by one or more other heteroatom containing groups.

Potential substituents on the alkane portion of the sulfonic acid include, for example, alkyl, hydroxyl, alkoxy, acyloxy, keto, carboxyl, amino, substituted amino, nitro, sulfenyl, sulfinyl, sulfonyl, mercapto, sulfonylamido, disulfonylimido, phosphinyl, phosphonyl, carbocyclic and/or heterocyclic groups. Such sulfonic acids preferably include, for example, methanesulfonic acid, ethanesulfonic acid, propanesulfonic acid, butanesulfonic acid, isethionic acid (2-hydroxyethanesulfonic acid), methionic acid (methanedisulfonic acid), 2-aminoethanesulfonic acid and sulfoacetic acid, among others.

The aromatic sulfonic acids covered include substituted or unsubstituted benzenesulfonic acid having monosulfonate or polysulfonate functionalization. Covered aromatic sulfonic acid compounds include, for example, p-toluenesulfonic acid, phenolsulfonic acid, benzenesulfonic acid, toluenedisulfonic acid and benzenedisulfonic acid, among others.

The sulfonic acid is generated by electrowinning the metal from the metal alkanesulfonate or metal aromatic sulfonate solution in either an undivided or a divided cell. The acid generation proceeds by an electrochemical reaction at the inert anode of the electrowinning cell and/or by hydrolytic reactions of an anodically generated higher oxidation state of the metal cation. In cases where the metal cation has little tendency to be further oxidized at the anode, e.g., Cu(II), Zn(II), the totality of the acid generation process involves the removal of the metal by electrowinning at the cathode in association with generation of the sulfonic acid (protons) at the anode. This process can be illustrated by the consideration of the electrowinning of cupric alkanesulfonate in an undivided cell. In this case, the deposition of copper is the primary cathode process, and the generation of protons/oxygen is the primary anode process.

For the electrowinning process described in this invention to operate effectively, the current density must range from between about 1 ASF (amps per square foot) and about 4000 ASF, and more preferably between about 10 ASF and about 400 ASF.

The isolation of a substantially pure sulfonic acid from an oxidation based preparation, purification and/or recovery process, such as any of the anodic oxidation processes described in this invention, is not guaranteed, and the obtention of pure sulfonic acid is not an inherent result of such oxidation processes. A number of oxidation based preparation and purification processes for sulfonic acids are known to over-oxidize a significant portion of the sulfonic acids present to sulfuric acid. Proell describes a number of oxidative sulfonic acid production and purification methods which produce in excess of 2% sulfuric acid in the final sulfonic acid products (see e.g., U.S. Pat. No. 2,489,318). For the purposes of the present invention, the sulfonic acids produced must endure an increase in sulfuric acid and/or sulfate content of less than 1% by weight relative to the generated sulfonic acid in order to be considered generally useful. Additionally, previously reported electrowinning processes which employ electrolytes containing some sulfonic acid have not produced substantially pure sulfonic acid products which are generally useful. In U.S. Pat. No. 4,944,851 for example, a final product with in excess of 10 g/L of total reducible metal content (reducible metals are defined as all those metals not in groups IA, IIA, IIIA, IIIB, IVB, VB, and VIB of the periodic table) is reported. Such high metal content products are useful in certain specific applications, such as the regenerated stripper described in the patent, but high metal content sulfonic acid solutions are not appropriate for general reuse. For the purposes of the present invention, the generated sulfonic acids must contain less than 10 g/L and more preferably less than 2 g/L and most preferably less than 200 ppm of total reducible metal content in order to be considered generally useful.

In cases where the metal cation of the organosulfonate salt has easily accessible higher oxidation states, the acid generation process may involve both the anodic generation of acid by the electrolysis of water (or some other hydroxylic solvent) and the hydrolytic generation of acid by the reaction of anodically produced higher oxidation states of the metal cation with water (or some other hydroxylic solvent). Metal cation hydrolysis can be defined as the reaction of a metal cation with water (or some other hydroxylic solvent) to yield a metal oxide species and acid. A large number of representative metal cation hydrolysis reactions are described in the text book, "The Hydrolysis of Cations" by C. F. Baes and R. E. Mesmer (Krieger Publishing Company, Malabar, Fla., copyrighted in 1976, reprinted in 1986). In general, the higher oxidation states of metal cations are more prone to hydrolysis than are the lower oxidation states. In the system described herein, the extent of hydrolytic acid generation depends upon both the tendency for the metal cation of the sulfonate salt to be oxidized to a higher oxidation state and on the tendency for this higher oxidation state of the metal cation to hydrolyze. The aqueous solubility of hydrolyzed metal cations (metal oxide species) is strongly pH dependent. Under conditions where the oxidized metal cation of the organosulfonate salt is partially hydrolyzed but still soluble, the undivided cell electrowinning process of this invention will proceed, as in the case where hydrolysis does not occur, until all the metal has been cathodically deposited out of the solution. Under conditions where the oxidized metal cation of the sulfonate salt is hydrolyzed and insoluble, the proper practice of this invention requires that said insoluble hydrolysis product be removed by an appropriate technique (usually filtration). In some cases, metal cation hydrolysis products will deposit on the anode and/or cathode surface. Such electrode deposits are not problematic as long as they are conductive, but passivation can result when deposited hydrolysis products (i.e., metal oxides) are electrically insulating.

The process of this invention can also be carried out in a separated two compartment electrochemical cell. Electrochemical cell separation can be achieved with either a non-selective porous material such as a glass frit or with a selective device such as a charge transfer membrane. The use of a non-selective separator is optimal when some partitioning of the electrochemical cell is helpful but rigorous separation is not required. The use of a charge transfer type membrane separator is optimal when rigorous separation of the electrochemical cell is required. When charge transfer membrane separation is used, either the metal electrodeposition process combined with anodic acid generation (organosulfonate salt in the catholyte) or the metal cation oxidation process combined with hydrolytic acid generation (organosulfonate salt in the anolyte) will be predominant. The charge transfer membrane separator will prevent direct contact of the metal organosulfonate solution with one of the electrodes, and only one of the two acid generation modes will thus be allowed. Four charge transfer membrane separated cell modifications are possible:

I) Metal organosulfonate solution in the cathode compartment with a cation transfer membrane
II) Metal organosulfonate solution in the cathode compartment with an anion transfer membrane
III) Metal organosulfonate solution in the anode compartment with a cation transfer membrane
IV) Metal organosulfonate solution in the anode compartment with an anion transfer membrane In Modification I, the metal sulfonate solution is charged into the cathode compartment of the divided electrochemical cell, and the electrochemical process is optimized for electrodeposition of metal on the cathode and for oxygen evolution on the anode. The protons which are formed by the anode process pass through the cation transfer membrane into the cathode compartment. Upon completion, the organosulfonic acid is contained in the catholyte. This type of process is ideal for regenerating a used plating bath which operates a dissolving anode at a higher current efficiency than the plating cathode. In such situations, the metal content of the plating bath is increased at the expense of the free acid content. By electrowinning a used plating solution which is high in metal and low in free acid in the manner described above, one can reduce the excess metal content and raise the free acid content to acceptable levels. Thus, Modification I can be used to recondition metal rich sulfonic acid based plating baths. Note that modification I is, with respect to acid purity, no better than simple electrowinning in an undivided cell. However, modification I is useful when the solution in which sulfonic acid is being regenerated also contains compounds which are sensitive to oxidation (e.g. an electroplating solution which also contains valuable reducing agents).

In Modification II, the metal organosulfonate solution is charged into the cathode compartment of the divided electrochemical cell, and the electrochemical process is again optimized for electrodeposition of metal on the cathode and for oxygen evolution on the anode. The sulfonate anions which are freed up by the electrodeposition of the metal pass through the anion transfer membrane into the anolyte compartment. In this modification, the protons which are formed by the anode process remain in the anolyte compartment. Upon completion, a very pure organosulfonic acid is contained in the anolyte. This modification is most useful in situations where very pure recovered organosulfonic acid is desired.

Under certain circumstances, such as are occasionally found with used plating baths, an aqueous solution of metal organosulfonate may contain an undesired excess of free sulfonic acid. In this case, electrowinning as described by Modification II can oftentimes be optimized for selective removal of the free acid. If the cathodic electrode process can be adjusted so as hydrogen formation predominates, a situation which is particularly applicable for active metals, then the net result of the modification II electrowinning process will be the movement of free acid from the catholyte into the anolyte. One must remember that following the removal of some amount of free acid, metal deposition may begin to occur. Thus, an aqueous solution composed of a mixture of metal organosulfonate and free organosulfonic acid may be treated via Modification II for the recovery of pure free acid with simultaneous regeneration of a metal organosulfonate solution depleted of undesired free acid. Electrowinning by Modification II for the selective removal of free sulfonic acid from a mixed solution of organosulfonic acid and metal organosulfonate salt is particularly well suited to aqueous solutions of iron, nickel and/or cobalt organosulfonate, as these first row Group VIII transition metals allow for easy adjustment, by pH and/or potential modification, of the cathode process so as hydrogen generation is predominant.

In another application of Modification II, the reduction of water, generation of hydrogen and hydroxide, at the cathode can be used to sludge, as an insoluble metal hydroxide/oxide, the metal organosulfonate salt contained in the catholyte compartment with concomitant formation of organosulfonic acid in the anolyte compartment. Thus, metal salts which can not be made to electrodeposit metal at near neutral pH (e.g., Ni under some conditions) can be treated by the methods described for Modification II with the result still being the generation of pure organosulfonic acid in the anolyte compartment. The major difference between Modification II with cathodic metal electrodeposition and metal oxide sludge whereas with metal electrodeposition the final form of the metal is typically conveniently removed metallic coating on the cathode surface.

In Modification III, the metal organosulfonate solution is charged into the anolyte compartment of the divided electrochemical cell and the electrochemical process is optimized for the cathodic production of hydrogen and the anodic oxidation of the metal cation to a hydrolytically active higher oxidation state (note that only certain oxidation states of certain metals are susceptible to this type of oxidation). Some of the protons which are formed by hydrolytic reactions in the anolyte pass through the cation transfer membrane to react with the hydroxide formed by the cathodic hydrogen evolution reaction. The balance of the protons formed remain in the anolyte. For this variation of Modification III to be useful, the hydrolyzed metal cation must quantitatively precipitate either as an oxide sludge which can be filtered from the final product or as an adherent oxide coating which remains on the anode surface. Upon completion, the organosulfonic acid is contained in the anolyte compartment. Note that this version of modification III is, with respect to acid purity, no better than simple electrowinning in an undivided cell. This version of modification III will favor high valent metal ion hydrolysis over metal electrodeposition as the primary mode of metal consumption, but metal ion oxidation will not always be the exclusive mode. This version of modification III proceeds with the transfer of some amount, normally a small amount, of metal cations through the cation-exchange membrane, and this metal cation transfer will in turn allow for some metal to be electrodeposited at the cathode.

In a second variation of Modification III, the electrode processes are adjusted for oxygen formation (protons) on the anode and hydrogen formation (hydroxides) on the cathode. Initially, most of the ionic current across the membrane is carried by the metal cations, and metal salts transfer to the catholyte as organosulfonic acid builds-up in the anolyte. As the concentration of acid increases in the anolyte compartment, the percentage of ionic current carried by proton transport across the membrane will increase. Thus, the efficiency of the process decreases continuously as it proceeds. In those cases where relatively small amounts of impure acid need to be recovered and/or where high current inefficiency is tolerable, this variation of Modification III is acceptable, but modification II wherein the metal salt solution is directly charged into the catholyte is usually a more preferable choice. Note that this version of modification III is, with respect to acid purity, no better than simple electrowinning in an undivided cell. This version of modification III might be useful when the solution in which sulfonic acid is being regenerated also contains compounds which are sensitive to reduction (e.g. an electroplating solution which also contains valuable oxidizing agents).

In Modification IV, the metal organosulfonate solution is charged into the anolyte compartment of the divided electrochemical cell and the electrochemical process is again optimized for the cathodic production of hydrogen and the anodic oxidation of the metal cation to a hydrolytically unstable high valent state. Beyond this, the process can be described and varied according to the general principles already outlined for Modifications I through III. Again it should be noted that modification IV is, with respect to acid purity, no better than simple electrowinning in an undivided cell, but modification IV is useful when one wants the totality of the acid generation process to involve metal cation hydrolysis. This exclusivity is guaranteed, at least theoretically, by the use of the anion-exchange membrane (i.e., a membrane which allows no metal to enter the catholyte compartment).

Continuous versions of and multi-compartment versions of the above processes, including variations employing bipolar membranes, are considered to be within the scope of this invention disclosure.

A preferred embodiment of this invention is a continuous process incorporating an electrowinning cell divided by an anion exchange membrane and fitted with a source of high volume continuous catholyte feed such that the dissolved metal content in the catholyte is maintained at close to optimum levels.

A variation on this preferred embodiment is the use of a multi-compartment electrowinning cell divided into a number of alternating anolyte and catholyte chambers separated by anion exchange membranes. As opposed to a two-chamber cell where metal deposition can only occur on one side of the cathode, the use of multiple chambers allows for the use of one or more cathodes with metal deposition on both sides of the cathode(s), thereby increasing the efficiency of the process. The number and volume of the individual chambers employed in any given application would depend on the volume of catholyte to be treated, the catholyte metal salt concentration, and the volume and concentration desired for the recovered organosulfonic acid.

For optimum efficiency in metal deposition and acid recovery, the number of anolyte chambers should be one more than the number of catholyte chambers. Such a multi-compartmental cell apparatus used in continuous process would be comprised of the multi-compartmental electrowinning cell; a catholyte feed reservoir for containing a catholyte which can be continuously recirculated through the catholyte chambers by a recirculating means, for example, a pump; a means for introducing feed water continuously into all anolyte chambers; and an acid-receiving reservoir into which the generated organosulfonic acid effluent from the anolyte chambers can be collected. The continuous recirculation through the catholyte chamber serves to improve the agitation within the catholyte chamber and permits operation at optimal current density. The specific design of the entire process and of the electrowinning cell would depend on the particular application.

The continuous process may include charging the catholyte reservoir with a concentrated aqueous solution of metal organosulfonate then continuously recirculating this solution through the catholyte chamber during electrolysis under constant current conditions, whereupon the metal would be deposited onto the cathode. The liberated organosulfonate anion would migrate across the membrane and associate with protons being generated at the anode. Simultaneously with the electrolysis, water would be continuously introduced into anolyte chamber, and generated dilute organosulfonic acid would be removed from the anolyte chamber and collected in the acid-receiving reservoir.

In that one effect of the electrowinning process is the depletion of the catholyte in dissolved metal and organosulfonate ions, the depleted catholyte solution can be used to dissolve additional solid metal organosulfonate at ambient or elevated temperatures. The resulting rejuvenated solution can then be recycled into the electrowinning process so as to maintain the catholyte metal organosulfonate concentration at near optimum levels. Alternatively, all or some part of the depleted catholyte could be removed from the process and replaced with fresh metal organosulfonate solution. These recharging procedures could be incorporated as integral or separate parts of the continuous electrowinning process.

Depending on the application and design, the catholyte reservoir could also serve as a dissolution tank for solid metal organosulfonate salts, and as a process surge tank to accommodate variable production levels of the feed metal organosulfonate salt solution.

Also depending on the application and design, the acid receiving reservoir could serve as a concentrating vessel wherein water is stripped from the generated organosulfonic acid, thereby generating a more concentrated organosulfonic acid product.

The process could optionally be appropriately instrumented or otherwise monitored in such a way that the specific processing steps operate in the most efficient manner. Key operational parameters might include the concentration of the metal organosulfonate salt in the catholyte, the concentration of organosulfonic acid in the anolyte, residual metal concentration in the anolyte, concentration of organosulfonic acid product in the acid receiver/stripper, and temperatures within the various vessels and chambers.

If cathodic hydrogen formation is not desired and the metal being deposited has a tendency to promote hydrogen formation (i.e., low hydrogen overvoltage), then a method of continuously removing the deposited metal from an underlying cathode surface with a high hydrogen overvoltage is desirable. For instance, stainless steel has the requisite hydrogen overvoltage for the efficient electrowinning of a number of metals, and stainless steel oftentimes allows for the production of loose and non-adherent electrodeposits. By constantly removing a non-adherent electrodeposit with a low hydrogen overvoltage from an underlying cathode surface with a high hydrogen overvoltage (e.g., by gravity based dislodgement of electrodeposited metal particles) one can greatly reduce the problems associated with excessive hydrogen formation. Ideally, such dislodged metal particles are produced as relatively large pieces which can be easily collected in a holding area. Conversely, the production of fine metal powders is oftentimes not advisable, as such powders can become suspended in the electrowinning solution causing clogging and short-circuiting of the cell. Excessive hydrogen evolution can be a problem in undivided cell electrowinning and in Modifications I & II (described above) of divided cell electrowinning. In Modifications III & IV (described above) of divided cell electrowinning, hydrogen evolution is the desired cathode reaction, and, when hydrogen evolution is desired, a cathode material with a low hydrogen overvoltage should be employed. Conversely, when hydrogen evolution is not desired, a cathode material with a high hydrogen overvoltage should be employed.

In general, the occurrence of side-reactions is to be expected in any electrochemical process, and any modification by side-reactions of the procedures described in this invention is intended to be covered by this invention.

It is possible to use this invention for the recovery of sulfonic acid from an old, contaminated and/or off-specification sulfonic acid based electroplating solution. The invention is also applicable when relatively pure metal alkanesulfonates can be isolated from such plating solutions. The isolation of a metal alkanesulfonate from a plating solution can be achieved by numerous methods including ion-exchange, selective crystallization, evaporation, etc., and an application of particular importance is the recovery of pure sulfonic acid from ferrous and/or ferric sulfonate salts isolated from iron contaminated plating baths. Iron contamination in such systems normally results from corrosion of ferrous based alloys which are plated in the baths.

It is also possible to use this invention as part of a primary process for the manufacture of organosulfonic acids.

It is also possible to combine the novel electrowinning process described in this application with the nitric acid oxidation of metal mercaptide salts for the ultimate production of free alkanesulfonic acid. (M=some metal cation).

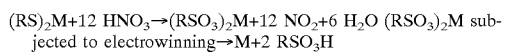
jected to electrowinning→M+2 RSO$_3$H

Furthermore, any method for the direct preparation of a metal organosulfonate salt of a VIB, VIIB, VIIIB, IB, IIB and/or VA metal can be combined with the novel electrowinning method described herein as a means for the primary production of an organosulfonic acid.

In some cases, useful organosulfonic acid recovery can be obtained with a purely chemical variation of the above described electrowinning processes. For those metal organosulfonate compounds with metal cations having hydrolytically reactive higher oxidation states, useful organosulfonic acid recovery can sometimes be obtained by simple treatment of a solution of the salt with an appropriate oxidizing agent such as hydrogen peroxide and/or oxygen.

Operable and Preferred Limits:

| Parameter | Operable Range | Preferred Range |
|---|---|---|
| Temperature | 2 to 110° C. | 15 to 70° C. |
| Current Density | 1 to 4000 ASF (ASF = Amps/Sq.Ft.) | 10 to 400 ASF |
| Agitation | None to vigorous | Vigorous |
| Metal Organosulfonate Concentration (Moles/L) | 0.01 M to 10 M | 0.1 M to 4 M |
| Anode Composition | Dissolving or inert conductive material | IrO$_2$ Coated Ti or other inert anode material |
| Cathode Composition | Conductive material | Metal or conductor with high hydrogen overvoltage |
| Geometric Anode Surface, Area per Liter of Solution | 1 to 10,000 cm$^2$/L | 100 to 10,000 cm$^2$/L |
| Geometric Cathode Surface, Area per Liter of Solution | 1 to 10,000 cm$^2$/L | 100 to 10,000 cm$^2$/L |
| Addition Agents for Improvement of Electrodeposited Metal Quality | Any as needed | Any as needed |
| Any as needed | Any as needed | Any as needed |

The following examples are set forth to demonstrate the invention:

EXAMPLE 1

An undivided electrowinning cell is charged with 250 ml of Cu(OMs)$_2$(aq) solution [52 g/L as Cu metal]. The cell is fitted with a copper cathode (exposed geometric area=6"$^2$) and a 316 SS anode (exposed geometric area=5"$^2$) A constant current of 4 A is passed through the cell for 3 h followed by a constant current of 2 Amps for 1 h. The cell voltage hovers at about 5 V throughout the electrolysis. A total of 0.52 moles of electrons are passed (14 Amp-hours= 50,400 coulombs, 50,400 coulombs divided by 96,500 coulombs per mole of electrons=0.52 mole). The volume of the solution is maintained constant by additions of DI water. The copper concentration is reduced from an initial level of 52 g/L [as Cu] to a final value of 0.268 g/L [as Cu] (app. 1.6 N decrease in [Cu]) while the MSA(aq) concentration is increased from near 0 g/L up to 134 g/L (approximately 1.4 N increase in acid). The cathode process is approximately 80% efficient overall for the reduction of copper. The anode process produced oxygen/acid along with some dissolved Fe(II), Fe(III) and Ni(II). The dissolved metals are produced by oxidative dissolution of the anode material. The anode process is approximately 70% efficient for the production of acid. In an acid recovery operation, it is usually not desirable to have the oxidative dissolution of metal ions from the anode, and anodes composed of materials more robust than stainless steel are recommended.

EXAMPLE 2

A series of electrowinning experiments are performed in an undivided electrochemical cell charged with 250 ml of an appropriate aqueous solution of a metal alkanesulfonate salt. The cell is fitted with a stainless steel cathode and an $IrO_2$ coated titanium inert anode. The average inter-electrode spacing is 2". A constant current of about 3 A (cathode current density=60 ASF, anode current density=105 ASF) is passed through the cell for various lengths of time. The solution temperature is allowed to rise, through resistive heating, over the first hour of electrolysis to about 35° C. where it remained throughout the rest of the experiment. The volume of the solution is maintained constant throughout the electrolysis by occasional additions of DI water. Following the passage of an appropriate amount of charge, the solutions are filtered and analyzed for metal and acid content. Representative data is tabulated below:

| | EXPERIMENTAL DATA FROM ELECTROWINNING EXPERIMENTS WITH METAL ALKANESULFONATES | | | | | |
|---|---|---|---|---|---|---|
| Metal[a] | [Metal] (initial) g/L (M)[b] | [Metal] (final) g/L (M)[c] | [Acid] (initial) mequiv/g[d] | [Acid] (final) mequiv/g[e] | % Completion M/A[f] | % Current Efficiency[g] |
| Palladium (MSA)[h] | 4.5 (0.04) | 0 (0) | 0.03 | 0.15 | 100%/100+% | 57% |
| Silver (MSA) | 109 (1.01) | 3 (0.03) | 0.02 | 0.97 | 97%/94% | 53% |
| Copper (PSA) | 63 (0.99) | 0.2 (0.003) | 0.01 | 2.01 | 99%/100% | 79% |
| Tin (ESA) | 59 (0.50) | 0.4 (0.003) | 0.05 | 1.01 | 99%/96% | 85% |
| Lead (MSA) | 184 (0.89) | 0.4 (0.002) | 0.01 | 2.01 | 100%/100+% | 130%[i] |
| Nickel (PSA) | 51 (0.87) | 36 (0.61) | 0.02 | 0.55 | 29%/31% | 17% |
| Cobalt (ESA) | 55 (0.93) | 40 (0.68) | 0.01 | 0.68 | 27%/36%% | 14% |
| Cadmium (PSA) | 66 (0.59) | 0.1 (0.001) | 0.04 | 1.61 | 100%/100+% | 46% |
| Iron (MSA) | 54 (0.97) | 46 (0.82) | 0.02 | 1.01 | 15%/51% | 81% |
| Iron/Tin[j] (MSA) | 26 (0.46) | 26 (0.46) | 0.22 | 0.36[k] | 0%/32% | 14%[l] |
| Zinc (PSA) | 56 (0.86) | 18 (0.27) | 0.03 | 1.21 | 68%/69% | 23% |
| Zinc[m] (ESA) | 66 (1.01) | 5 (0.08) | 0.01 | 1.54 | 92%/81% | 52% |

Notes:
[a] Metals were dissolved in DI $H_2O$ as Pd (II), Ag (I), Cu (II), Sn (II), Pb (II), Ni (II), Co (II), Cd (II), Fe (II)/(III), Zn (II).
[b] The initial concentration of the metal before electrowinning expressed as g metal per liter of solution with molarity in parenthesis; by ICP/emission.
[c] The final concentration of the metal following electrowinning expressed as g metal per liter of solution with molarity in parenthesis; by ICP/emission.
[d] The initial concentration of strong acid before electrowinning expressed as moles $H^+$ per Kg solution; by pH titration.
[e] The final concentration of strong acid after electrowinning expressed as moles $H^+$ per Kg solution; by pH titration.
[f] The % completion of the process (M/A) based on: M - The amount of metal removed from solution relative to the total amount of metal originally present. A - The amount of acid present in the final solution relative to the total amount possible for the amount of metal removed by electrodepositon. Values of A which are greater than 100% are the result of measurement uncertainties, unknown variables and/or the formation of soluble/suspended high valent metal oxide compounds. High valent metal oxide compounds yield excess acid upon formation, but the metal compounds also continue to remain in solution. The formation of high valent metal oxide compounds results in net acid production without the metal being removed from solution. Values of A which are less than 100% result from measurement uncertainty.
[g] The % current efficiency of the process based on the amount of metal removed. The current efficiency was calculated as mn/q (m = moles metal removed, n = metal valence, q = mole equivalents of charge passed). The total charge passed (TCP), in coulombs, can be calculated as {(moles metal removed) × (metal valence) × (1/current efficiency) × (96,487)}; the total electrolysis time, in seconds, can be calculated as {(TCP)/(3)}, a current of 3 A was used.
[h] MSA = methanesulfonate, ESA = ethanesulfonate, PSA = propanesulfonate.
[i] A current efficiency of greater than 100% was obtained because lead was being removed at both electrodes.
[j] Sample obtained from an operational Fe removal system; (analysis = 0.46M Fe, 0.08M Sn, 0.22M MSA).
[k] This acid was generated by the efficient electrowinning of the small amount of tin which was present in the solution.
[l] UD = undefined; acid recovery values and current efficiency relative to the iron concentration is undefined.
[m] This experiment employed a special high surface area carbon cathode for the final stages of the electrowinning.

EXAMPLE 3

A divided cell electrowinning apparatus is fitted with a stainless steel cathode (2" by 4"), an iridium oxide coated titanium mesh anode (2" by 6") and an ESC 7001 anion exchange membrane. The catholyte chamber is charged with 1 liter of a 0.47 molar aqueous solution of ferrous/ferric methanesulfonate. The anode chamber is charged with 1 liter of 0.1% aqueous solution of methanesulfonic acid (approximately 0.01 M). A current of 3 Amps, at about 14 Volts, is passed for 24 hours (2.7 Faradays of charge, cathode current density=54 ASF, anode current density=90 ASF, membrane current density=27 ASF). The compositions of the catholyte and anolyte before and after electrolysis are as follows:

| Chamber[a] | [Iron] (initial) g/L (M)[b] | [Iron] (final) g/L (M)[c] | [Acid] (initial) m[d] | [Acid] (final) m[e] | % Complete[f] | % Current Efficiency |
|---|---|---|---|---|---|---|
| catholyte | 26.2 (0.47) | 0.9 (0.02) | 0.02 | 0.02 | 96% | 33%[g] |
| anolyte | 0 (0) | 0 (0) | 0.01 | 0.88 | 97% | 33%[h] | a–h see notes below

An electrowinning experiment is conducted in a manner identical to that described above except that the catholyte chamber is charged with an aqueous solution containing 0.47 M Fe(OMs)$_2$, 0.1 M Sn(OMs)$_2$ and 0.22 M MSA(aq), and the anolyte chamber is charged with a 0.6% aqueous solution of MSA(aq). A current of 3 Amps, at about 20 Volts, is passed for 30 hours (3.3 Faradays of charge, cathode current density=54 ASF, anode current density=90 ASF, membrane current density=27 ASF). The compositions of the catholyte and anolyte before and after electrolysis are as follows:

| Chamber[a] | [Iron] (initial) g/L (M)[b] | [Iron] (final) g/L (M)[c] | [Acid] (initial) m[d] | [Acid] (final) m[e] | % Complete[f] | % Current Efficiency |
|---|---|---|---|---|---|---|
| catholyte | 26.4 (0.47) | 0.9 (0.02) | 0.20 | 0.01 | 97% | 39%[g] |
| anolyte | 0 (0) | 0 (0) | 0.06 | 1.12 | 86% | 39%[h] |

[a]The chamber of the divided electrowinning cell.
[b]The initial concentration of the metal before electrowinning expressed as grams metal per liter of solution with molarity in parenthesis; determination by ICP/emission analysis.
[c]The final concentration of the metal following electrowinning expressed as grams metal per liter of solution with molarity in parenthesis; determination by ICP/emission analysis.
[d]The initial concentration of strong acid before electrowinning expressed as moles per Kg of solution; by pH titration.
[e]The final concentration of strong acid after electrowinning expressed as moles per Kg of solution; by pH titration.
[f]The % completion based on the amount of metal removed for the catholyte. The % completion based on the amount of acid finally present relative to the total amount possible for the anolyte.
[g]The % current efficiency of the cathode process based on the amount of metal removed per mole of current passed.
[h]The % current efficiency of the anode process (oxygen evolution with regeneration of acid) was close to 100%; the observed inefficiency (apparent inefficiency) was due to the leakage of hydronium ion across the membrane.

EXAMPLE 4

A divided cell electrowinning apparatus as described in Procedure 2 is used for this experiment. The catholyte chamber is charged with 1 liter of a spent electroless nickel bath (5 g/L Ni$^{+2}$, 40 mL/L lactic acid, 30 g/L hypophosphite) in which the pH has been raised from 4.8 to 8.5 with ammonia (color changed from green to blue). The anolyte chamber is charged with 1 liter of a 1% aqueous solution of methanesulfonic acid (approximately 0.1 M). A current of 1 Amps, at about 10 Volts, is passed for 32 hours (1.2 Faradays of charge, cathode current density=18 ASF, anode current density=30 ASF, membrane current density=9 ASF). The compositions of the catholyte and anolyte before and after electrolysis are as follows;

| Chamber | [Ni] (initial) g/l (M) | [Ni] (final) g/l (M) | [Acid] (initial) mequiv/gram | [Acid] (final) mequiv/gram |
|---|---|---|---|---|
| catholyte | 5 (0.08) | 0 | 1.38 | 0 |
| anolyte | 0 | 0 | 0.13 | 1.67 |

The acid in the anolyte compartment at the end of the electrowinning experiment was composed of 9% acetic acid, 65% methanesulfonic acid and 26% lactic acid.

EXAMPLE 5

A divided cell electrowinning apparatus as described in Procedure 2 is used in this experiment. The catholyte chamber is charged with 1 liter of a 60 g/L (as Ni) nickel methanesulfonate solution (pH=5). The anolyte chamber is charged with 1 liter of a 0.5% aqueous solution of methanesulfonic acid (approximately 0.05 M). A current of 2 Amps, at about 6 Volts, is passed for 28 hours (2.1 Faradays of charge, cathode current density=36 ASF, anode current density=60 ASF, membrane current density=18 ASF). The compositions of the catholyte and anolyte before and after electrolysis are as follows;

| Chamber[a] | [Ni] (initial) g/L (M)[b] | [Ni] (final) g/L (M)[c] | [Acid] (initial) m[d] | [Acid] (final) m[e] | % Complete[f] | % Current Efficiency |
|---|---|---|---|---|---|---|
| catholyte | 55.9 (0.95) | 18.2 (0.31) | 0.01 | 0.01 | 67% | 61%[g] |
| anolyte | 0.0 (0) | 0.034 (0) | 0.05 | 1.10 | 56% | 50%[h] |

[a]The chamber of the divided electrowinning cell.
[b]The initial concentration of the metal before electrowinning expressed as grams metal per liter of solution with molarity in parenthesis; determination by ICP/emission analysis.
[c]The final concentration of the metal following electrowinning expressed as grams metal per liter of solution with molarity in parenthesis; determination by ICP/emission analysis.
[d]The initial concentration of strong acid before electrowinning expressed as moles per Kg of solution; by pH titration.
[e]The final concentration of strong acid after electrowinning expressed as moles per Kg of solution; by pH titration.
[f]The % completion based on the amount of metal removed for the catholyte. The % completion based on the amount of acid finally present relative to the total amount possible for the anolyte.
[g]The % current efficiency of the cathode process based on the amount of metal removed per mole of current passed.
[h]The % current efficiency of the anode process (oxygen evolution with regeneration of acid) was close to 100%; the observed inefficiency (apparent inefficiency) was due to the leakage of hydronium ion across the membrane.

In this example, nickel is not deposited on the cathode as nickel metal. Instead, hydroxide and hydrogen are generated at the cathode resulting in the precipitation of nickel hydroxide type species with net acid generation in the anolyte. The nickel sludge which precipitates in the cathode compartment could be removed by filtration on a regular schedule.

EXAMPLE 6

The robustness of aqueous alkanesulfonic acid electrolytes is assessed by subjecting 10% aqueous solutions of MSA (approximately 1 M) to 24 hours of electrolysis (production of hydrogen on the cathode, production of oxygen on the anode) at various current densities in an undivided cell. The cathode is a piece of polished silver. The anode is an IrO$_2$ coated titanium mesh. The increase in the sulfate concentration of MSA solutions following 24 hours of electrolysis at various current densities is tabulated below:

| Current Density (ASF) | Sulfate Concentration (ppm) |
|---|---|
| Cathode = 32 ASF, Anode = 20 ASF | 12 |
| Cathode = 64 ASF, Anode = 40 ASF | 12 |
| Cathode = 96 ASF, Anode = 60 ASF | 14 |

The low levels of sulfate formation, even after 24 hours of electrolysis at useful electrowinning current densities, illustrate the robustness of aqueous methanesulfonic acid based electrolytes. The small amount of sulfate which forms is produced via a poorly characterized anodic oxidation of both the MSA and certain low level impurities (e.g., dimethylsulfone) present in the MSA.

EXAMPLE 7

Continuous Process

A divided electrowinning cell is fitted with a stainless steel cathode (10.0 cm×6.9 cm), an iridium oxide coated titanium mesh anode (12.7 cm×9.0 cm), an anion exchange membrane (66.5 cm$^2$, ESC 7001, Electrosynthesis Company, Inc., Lancaster N.Y.), and inlet and outlet ports for both the catholyte and anolyte chambers. The cathode and anode are mounted such that the anode-membrane distance is 3 cm while the anode-cathode distance is 9.2 cm. The catholyte inlet and outlet ports are connected via tubing to a container which serves as the catholyte feed and effluent reservoir, with an in-line pump being installed on the feed line. Similarly, tubing is connected via a second in-line pump between the anolyte inlet port of the electrochemical cell and a second container which serves as the anolyte feed reservoir. Finally, tubing is connected from the anolyte outlet port to a third container which serves as the anolyte effluent receiver. This combination results in a system in which the catholyte solution can be pumped from and returned to the catholyte feed/effluent reservoir in a recirculating manner, the anolyte feed can be introduced into the anolyte chamber feed, and anolyte effluent can be withdrawn and collected. Constant liquid levels in the catholyte and anolyte chambers are maintained using overflow devices at the anolyte and catholyte chamber outlet ports. The working liquid volume of the catholyte chamber is 1300 mL while that of the anolyte chamber is 1370 mL.

Aqueous ferrous/ferric methanesulfonate solution (20 L, 54.9 g/L as Fe) is charged to the catholyte feed/effluent reservoir and continuously pumped to the catholyte chamber of the electrowinning cell at 330 mL/min.). Dilute 10.7% methanesulfonic acid (MSA) is charged to the anolyte chamber and distilled water is charged to the anolyte feed reservoir. The electrolysis is conducted at 4.0 Amperes constant current over 6.2 hours (0.92 Faradays of charge, cathode current density=54 ASF, anode current density=81 ASF, membrane current density=56 ASF) resulting in the deposition of ca. 8.1 g Fe deposited onto the cathode. Concurrent with the electrolysis, water is added to the anolyte chamber at a rate of 0.86 mL/minute and dilute MSA (124.1 g) is collected as the anolyte effluent. During the electrolysis, a slow decrease in cell voltage is observed (8.1–7.2 V, mean=7.4 V), along with a slow increase in anolyte temperature (22.9–26.8° C.) and a concomitant decrease in anolyte conductivity (340–323 mSiemen/cm). Analyses of the final anolyte solution (10.9% MSA) and the total anolyte effluent (11.5% MSA) indicate a net MSA production of 17.0 g, corresponding to 61% of the potential recoverable acid based on the amount of Fe deposited on the cathode.

Comparison of fe concentrations in the final anolyte solution (112 ppm), total collected anolyte effluent (130 ppm), and initial anolyte charge (135 ppm) indicate no net increase in the fe concentration of the anolyte solution during the electrolysis within the operational and analytical limits of this experiment.

What is claimed is:

1. A process for the generation of an alkanesulfonic or aromatic sulfonic acid from its soluble salt of a metal of Group VIB, VIIB, VIIIB, IIB, IB or VA of the periodic table comprising subjecting a solution of said salt in a solvent to:
   a) electrowinning in a cell employing a reactive cathode and an anode, electrogenerating, within an effective current density range, an alkanesulfonic or aromatic sulfonic acid from said salt at said anode and electrolytically producing a metal or metal compound from said salt adjacent or on said cathode, and substantially removing any metal containing precipitate from said solution, wherein the cell is undivided when the soluble salts are of metals of Group VA of the periodic table;
   b) electrolysis in a cell employing a reactive cathode and an anode, electrogenerating an oxidized species at said anode, said oxidized species reacting further to produce a sulfonic acid and a metal containing precipitate, and substantially removing said metal precipitate from the solution, or
   c) a chemical oxidizing agent in an amount sufficient to create an oxidized species which reacts further to produce a sulfonic acid along with a metal containing precipitate, and substantially removing said metal containing precipitate from the solution, or
   d) any combination of a), b) and c).

2. The process of claim 1 wherein said metal is manganese, rhenium, iron, rhodium, ruthenium, cobalt, iridium, nickel, palladium, platinum, copper, silver, gold, zinc, cadmium, mercury, antimony, bismuth or mixtures thereof.

3. The process of claim 1 wherein said alkanesulfonic acid has a linear or branched chain alkane group having from 1 to 8 carbon atoms and a monosulfonate or polysulfonate functionalization, and said aromatic sulfonic acid is a substituted or unsubstituted benzenesulfonic acid having a monosulfonate or polysulfonate functionalization.

4. The process of claim 1 wherein the electrowinning cell of a) or the electrolysis cell of b) is divided into an anode chamber and a cathode chamber by a charge transfer membrane.

5. The process of claim 4 wherein the membrane divided cell is separated into two or more compartments by cation transfer, anion transfer or bipolar membranes.

6. The process of claim 4 wherein the membrane divided cell is separated into two compartments by means of an anion transfer membrane and said solution of said salt is charged to the cathode chamber.

7. The process of claim 1 wherein the electrowinning cell of a) or the electrolysis cell of b) is divided by means of one or more porous separators.

8. The process of claim 7 wherein said porous separators include glass frits, ceramic frits or porous polymer sheets.

9. The process of claim 1 wherein the electrowinning of a) employs an inert anode which produces oxygen and acid by oxidation of the solvent.

10. The process of claim 9 wherein the solvent is water or a fluid mixture containing water.

11. The process of claim 9 wherein the solvent is hydroxylic and nonaqueous.

12. The process of claim 1 wherein the electrolysis of b) employs an inert anode which oxidizes species in said solution other than the solvent.

13. The process of claim 12 wherein the species oxidized is a metal cation.

14. The process of claim 1 wherein the said generation of alkanesulfonic or aromatic sulfonic acid is part of a primary process for the manufacture of said sulfonic acids from salts thereof.

15. The process of claim 1 wherein said solution of said salt is an inorganic electroplating solution and is nitrate-free.

16. The process of claim 15 wherein the salt of said inorganic nitrate-free solution is derived from a salt isolated from an electroplating solution.

17. The process of claim 16 wherein the isolation is by selective crystallization.

18. The process of claim 17 wherein said salt is an iron salt.

19. The process of claim 1 wherein the electowinning cell of a) or the electrolysis cell of b) is divided into an anode chamber and a cathode chamber by charge transfer membranes or by porous separators, and wherein the soluble salt is continuously introduced into the catholyte chamber.

20. The process of claim 1 wherein the electrowinning cell of a) or the electrolysis cell of b) is divided into an anode chamber and a cathode chamber by charge transfer membranes or by porous separators, and wherein organosulfonic acid is generated and is continuously removed as is it formed and its withdrawn volume replaced with water or dilute organosulfonic acid.

21. The process of claim 20 wherein the removed organosulfonic acid is concentrated by the removal of water.

22. The process of claim 1 wherein the electrowinning cell is divided into an anode chamber and a cathode chamber by charge transfer membranes or by porous separators, and wherein organosulfonic acid product obtained from the anode chamber is substantially free of metal ion impurities.

23. A process for the generation of an alkanesulfonic or aromatic sulfonic acid from its soluble salt of a metal of Group VIB, VIIB, VIIIB, IIB, IB or VA of the periodic table comprising subjecting a nonaqueous solution of said salt in a solvent to:

a) electrowinning in a cell employing a reactive cathode and an anode, electrogenerating an alkanesulfonic or aromatic sulfonic acid from said salt at said anode and electrolytically producing a metal or metal compound from said salt adjacent to or on said cathode, and substantially removing any metal containing precipitate from said solution.

24. A process for the generation of an alkanesulfonic or aromatic sulfonic acid from its soluble salt of a metal of Group VIB, VIIB, VIIIB, IIB, IB or VA of the periodic table comprising subjecting a solution of said salt in a solvent to:

a) electrowinning in a cell employing a reactive cathode and an anode, electrogenerating an alkanesulfonic or aromatic sulfonic acid from said salt at said anode and electrolytically producing a metal or metal compound from said salt adjacent to or on said cathode, and substantially removing any metal containing precipitate from said solution wherein the salt of said solution is derived from a salt isolated by selective crystallization from an electroplating solution.

\* \* \* \* \*